(12) United States Patent
Viswanathan (10) Patent No.: US 7,961,924 B2
(45) Date of Patent: Jun. 14, 2011

(54) METHOD OF THREE-DIMENSIONAL DEVICE LOCALIZATION USING SINGLE-PLANE IMAGING

(75) Inventor: Raju R. Viswanathan, St. Louis, MO (US)

(73) Assignee: Stereotaxis, Inc., St. Louis, MO (US)

(*) Notice: Subject to any disclaimer, the term of this patent is extended or adjusted under 35 U.S.C. 154(b) by 966 days.

(21) Appl. No.: 11/842,402

(22) Filed: Aug. 21, 2007

(65) Prior Publication Data

US 2008/0043902 A1    Feb. 21, 2008

Related U.S. Application Data

(60) Provisional application No. 60/838,958, filed on Aug. 21, 2006.

(51) Int. Cl.
*G06K 9/00* (2006.01)
*A61B 6/00* (2006.01)

(52) U.S. Cl. .......................................... 382/128; 378/20

(58) Field of Classification Search .................. 128/920; 378/4–9, 20, 901; 382/100, 128–134, 262; 345/424; 264/442; 434/272, 187, 188; 600/1–9, 600/30, 407, 424, 466, 433, 437, 408, 431; 601/1–2; 606/1; 604/903; 700/117; 706/45; 702/109; 703/2; 977/904

See application file for complete search history.

(56) References Cited

U.S. PATENT DOCUMENTS

| | | | |
|---|---|---|---|
| 5,654,864 A | 8/1997 | Ritter et al. | |
| 5,931,818 A | 8/1999 | Werp et al. | |
| 6,014,580 A | 1/2000 | Blume et al. | |
| 6,015,414 A | 1/2000 | Werp et al. | |
| 6,047,080 A * | 4/2000 | Chen et al. | 382/128 |
| 6,128,174 A | 10/2000 | Ritter et al. | |
| 6,148,095 A * | 11/2000 | Prause et al. | 382/131 |
| 6,148,823 A | 11/2000 | Hastings | |
| 6,152,933 A | 11/2000 | Werp et al. | |
| 6,157,853 A | 12/2000 | Blume et al. | |
| 6,212,419 B1 | 4/2001 | Blume et al. | |
| 6,241,671 B1 | 6/2001 | Ritter et al. | |
| 6,292,678 B1 | 9/2001 | Hall et al. | |
| 6,296,604 B1 | 10/2001 | Garibaldi et al. | |
| 6,298,257 B1 | 10/2001 | Hall et al. | |
| 6,304,768 B1 | 10/2001 | Blume et al. | |
| 6,315,709 B1 | 11/2001 | Garibaldi et al. | |
| 6,330,467 B1 | 12/2001 | Creighton, IV et al. | |
| 6,352,363 B1 | 3/2002 | Munger et al. | |
| 6,364,823 B1 | 4/2002 | Garibaldi et al. | |
| 6,375,606 B1 | 4/2002 | Garibaldi et al. | |
| 6,385,472 B1 | 5/2002 | Hall et al. | |
| 6,401,723 B1 | 6/2002 | Garibaldi et al. | |
| 6,428,551 B1 | 8/2002 | Hall et al. | |
| 6,459,924 B1 | 10/2002 | Creighton, IV et al. | |
| 6,475,223 B1 | 11/2002 | Werp et al. | |
| 6,501,848 B1 * | 12/2002 | Carroll et al. | 382/128 |

(Continued)

*Primary Examiner* — Samir A Ahmed
*Assistant Examiner* — Mehdi Rashidian
(74) *Attorney, Agent, or Firm* — Harness, Dickey & Pierce, P.L.C.

(57) ABSTRACT

A method and system for determining the three-dimensional location and orientation of a medical device distal end using a single-plane imaging system, using a computational model of the medical device and a transfer function for the medical device describing local device shape and orientation in response to user or computer determined inputs. The method allows guidance of an interventional medical system to a set of target points within the patient using a single-projection imaging system.

9 Claims, 8 Drawing Sheets

U.S. PATENT DOCUMENTS

| | | |
|---|---|---|
| 6,505,062 B1 | 1/2003 | Ritter et al. |
| 6,507,751 B2 | 1/2003 | Blume et al. |
| 6,522,909 B1 | 2/2003 | Garibaldi et al. |
| 6,524,303 B1 | 2/2003 | Garibaldi |
| 6,527,782 B2 | 3/2003 | Hogg et al. |
| 6,537,196 B1 | 3/2003 | Creighton, IV et al. |
| 6,542,766 B2 | 4/2003 | Hall et al. |
| 6,562,019 B1 | 5/2003 | Sell |
| 6,630,879 B1 | 10/2003 | Creighton, IV et al. |
| 6,662,034 B2 | 12/2003 | Segner et al. |
| 6,677,752 B1 | 1/2004 | Creighton, IV et al. |
| 6,702,804 B1 | 3/2004 | Ritter et al. |
| 6,733,511 B2 | 5/2004 | Hall et al. |
| 6,755,816 B2 | 6/2004 | Ritter et al. |
| 6,817,364 B2 | 11/2004 | Garibaldi et al. |
| 6,834,201 B2 | 12/2004 | Gillies et al. |
| 6,902,528 B1 | 6/2005 | Garibaldi et al. |
| 6,911,026 B1 | 6/2005 | Hall et al. |
| 6,940,379 B2 | 9/2005 | Creighton |
| 6,968,846 B2 | 11/2005 | Viswanathan |
| 6,975,197 B2 | 12/2005 | Creighton, IV |
| 6,980,843 B2 | 12/2005 | Eng et al. |
| 7,008,418 B2 | 3/2006 | Hall et al. |
| 7,010,338 B2 | 3/2006 | Ritter et al. |
| 7,019,610 B2 | 3/2006 | Creighton, IV et al. |
| 7,020,512 B2 | 3/2006 | Ritter et al. |
| 7,066,924 B1 | 6/2006 | Garibaldi et al. |
| 7,137,976 B2 | 11/2006 | Ritter et al. |
| 7,161,453 B2 | 1/2007 | Creighton, IV |
| 7,189,198 B2 | 3/2007 | Harburn et al. |
| 7,190,819 B2 | 3/2007 | Viswanathan |
| 7,211,082 B2 | 5/2007 | Hall et al |
| 7,248,914 B2 | 7/2007 | Hastings et al. |
| 7,264,584 B2 | 9/2007 | Ritter et al. |
| 7,599,730 B2 * | 10/2009 | Hunter et al. ............... 600/424 |
| 2001/0038683 A1 | 11/2001 | Ritter et al. |
| 2002/0019644 A1 | 2/2002 | Hastings et al. |
| 2002/0100486 A1 | 8/2002 | Creighton, IV et al. |
| 2002/0177789 A1 | 11/2002 | Ferry et al. |
| 2003/0125752 A1 | 7/2003 | Werp et al. |
| 2004/0006301 A1 | 1/2004 | Sell et al. |
| 2004/0019447 A1 | 1/2004 | Shachar |
| 2004/0030244 A1 | 2/2004 | Garibaldi et al. |
| 2004/0064153 A1 | 4/2004 | Creighton, IV et al. |
| 2004/0068173 A1 | 4/2004 | Viswanathan |
| 2004/0133130 A1 | 7/2004 | Ferry et al. |
| 2004/0147829 A1 | 7/2004 | Segner et al. |
| 2004/0157082 A1 | 8/2004 | Ritter et al. |
| 2004/0158972 A1 | 8/2004 | Creighton, IV et al. |
| 2004/0186376 A1 | 9/2004 | Hogg et al. |
| 2004/0249262 A1 | 12/2004 | Werp et al. |
| 2004/0249263 A1 | 12/2004 | Creighton, IV |
| 2004/0260172 A1 | 12/2004 | Ritter et al. |
| 2004/0267106 A1 | 12/2004 | Segner et al. |
| 2005/0004585 A1 | 1/2005 | Hall et al. |
| 2005/0020911 A1 | 1/2005 | Viswanathan et al. |
| 2005/0021063 A1 | 1/2005 | Hall et al. |
| 2005/0033162 A1 | 2/2005 | Garibaldi et al. |
| 2005/0043611 A1 | 2/2005 | Sabo et al. |
| 2005/0065435 A1 | 3/2005 | Rauch et al. |
| 2005/0096589 A1 | 5/2005 | Shachar |
| 2005/0113628 A1 | 5/2005 | Creighton, IV et al. |
| 2005/0113812 A1 | 5/2005 | Viswanathan et al. |
| 2005/0119556 A1 | 6/2005 | Gillies et al. |
| 2005/0119687 A1 | 6/2005 | Dacey, Jr. et al. |
| 2005/0182315 A1 | 8/2005 | Ritter et al. |
| 2005/0256398 A1 | 11/2005 | Hastings et al. |
| 2005/0273130 A1 | 12/2005 | Sell |
| 2006/0004382 A1 | 1/2006 | Hogg et al. |
| 2006/0009735 A1 | 1/2006 | Viswanathan et al. |
| 2006/0025676 A1 | 2/2006 | Viswanathan et al. |
| 2006/0025679 A1 | 2/2006 | Viswanathan et al. |
| 2006/0025719 A1 | 2/2006 | Viswanathan et al. |
| 2006/0036125 A1 | 2/2006 | Viswanathan et al. |
| 2006/0036163 A1 | 2/2006 | Viswanathan |
| 2006/0036213 A1 | 2/2006 | Viswanathan et al. |
| 2006/0041178 A1 | 2/2006 | Viswanathan et al. |
| 2006/0041179 A1 | 2/2006 | Viswanathan et al. |
| 2006/0041180 A1 | 2/2006 | Viswanathan et al. |
| 2006/0041181 A1 | 2/2006 | Viswanathan et al. |
| 2006/0041245 A1 | 2/2006 | Ferry et al. |
| 2006/0058646 A1 | 3/2006 | Viswanathan |
| 2006/0061445 A1 | 3/2006 | Creighton, IV |
| 2006/0074297 A1 | 4/2006 | Viswanathan |
| 2006/0079745 A1 | 4/2006 | Viswanathan |
| 2006/0079812 A1 | 4/2006 | Viswanathan |
| 2006/0094956 A1 | 5/2006 | Viswanathan |
| 2006/0100505 A1 | 5/2006 | Viswanathan |
| 2006/0114088 A1 | 6/2006 | Shachar |
| 2006/0116633 A1 | 6/2006 | Shachar |
| 2006/0144407 A1 | 7/2006 | Aliberto et al. |
| 2006/0144408 A1 | 7/2006 | Ferry |
| 2006/0145799 A1 | 7/2006 | Creighton, IV |
| 2006/0270915 A1 | 11/2006 | Ritter et al. |
| 2006/0270948 A1 | 11/2006 | Viswanathan et al. |
| 2006/0278248 A1 | 12/2006 | Viswanathan |
| 2007/0016010 A1 | 1/2007 | Creighton, IV et al. |
| 2007/0016131 A1 | 1/2007 | Munger et al. |
| 2007/0019330 A1 | 1/2007 | Wolfersberger |
| 2007/0021731 A1 | 1/2007 | Garibaldi et al. |
| 2007/0021742 A1 | 1/2007 | Viswanathan |
| 2007/0021744 A1 | 1/2007 | Creighton, IV |
| 2007/0030958 A1 | 2/2007 | Munger |
| 2007/0032746 A1 | 2/2007 | Sell |
| 2007/0038064 A1 | 2/2007 | Creighton, IV |
| 2007/0038065 A1 | 2/2007 | Creighton, IV et al. |
| 2007/0038074 A1 | 2/2007 | Ritter et al. |
| 2007/0038410 A1 | 2/2007 | Tunay |
| 2007/0040670 A1 | 2/2007 | Viswanathan |
| 2007/0043455 A1 | 2/2007 | Viswanathan et al. |
| 2007/0049909 A1 | 3/2007 | Munger |
| 2007/0055124 A1 | 3/2007 | Viswanathan et al. |
| 2007/0055130 A1 | 3/2007 | Creighton, IV |
| 2007/0060829 A1 | 3/2007 | Pappone |
| 2007/0060916 A1 | 3/2007 | Pappone |
| 2007/0060962 A1 | 3/2007 | Pappone |
| 2007/0060966 A1 | 3/2007 | Pappone |
| 2007/0060992 A1 | 3/2007 | Pappone |
| 2007/0062546 A1 | 3/2007 | Viswanathan et al. |
| 2007/0062547 A1 | 3/2007 | Pappone |
| 2007/0073288 A1 | 3/2007 | Hall et al. |
| 2007/0088197 A1 | 4/2007 | Garibaldi et al. |
| 2007/0135804 A1 | 6/2007 | Ritter |
| 2007/0137656 A1 | 6/2007 | Viswanathan |
| 2007/0146106 A1 | 6/2007 | Creighton, IV |
| 2007/0149946 A1 | 6/2007 | Viswanathan |
| 2007/0161882 A1 | 7/2007 | Pappone |
| 2007/0167720 A1 | 7/2007 | Viswanathan |
| 2007/0179492 A1 | 8/2007 | Pappone |
| 2007/0197899 A1 | 8/2007 | Ritter et al. |
| 2007/0197901 A1 | 8/2007 | Viswanathan |
| 2007/0197906 A1 | 8/2007 | Ritter |
| 2007/0225589 A1 | 9/2007 | Viswanathan |

* cited by examiner

METHOD OF THREE-DIMENSIONAL DEVICE LOCALIZATION USING SINGLE-PLANE IMAGING

CROSS-REFERENCE TO RELATED APPLICATION

This application claims priority to prior U.S. Provisional Patent Application Ser. No. 60/838,958, filed Aug. 21, 2006, the entire disclosure of which is incorporated herein by reference.

FIELD OF THE INVENTION

This invention relates to the three-dimensional localization of an interventional device using a single projection image and a model of the device. In particular, methods are described for the identification of the distal end of an interventional device with respect to a patient's anatomy, that rely on a model of the device mechanical properties as well as a model of the device control method.

BACKGROUND

Interventional medicine is the collection of medical procedures in which access to the site of treatment is made by navigation through one of the subject's blood vessels, body cavities or lumens. Interventional medicine technologies have been applied to manipulation of medical instruments such as guide wires and catheters which contact tissues during surgical navigation procedures, making these procedures more precise, repeatable, and less dependent on the device manipulation skills of the physician. Remote navigation of medical devices is a recent technology that has the potential to provide major improvements to minimally invasive medical procedures. Several presently available interventional medical systems for directing the distal end of a medical device use computer-assisted navigation and a display means for providing an image of the medical device within the anatomy. Such systems can display a projection of the medical device being navigated to a target location obtained from a projection imaging system such as x-ray fluoroscopy; the surgical navigation being effected through means such as remote control of the orientation of the device distal end and advance of the medical device.

SUMMARY

Embodiments of the present invention relates to methods for determining three-dimensional device location and orientation using a single-plane imaging system. The single plane imaging system remains at a fixed projection angle during at least the part of the intervention when the medical device is directed to contact target points within the anatomy of interest. In one embodiment of the present invention, a method comprises the steps of the user navigating a catheter or medical device to a location ("base point") suitable for subsequent medical intervention, obtaining information regarding the three-dimensional position of the base point and direction of the device at the base point through the acquisition of two or more projections at various angles or through other means, advancing and controlling the device beyond the base point through either the physician or automatically through actuation of device and system control vectors. Given a knowledge of the device mechanical properties, knowledge of the device control vector, and observation of the device in the patient on a single projection, the 3D location and orientation of the device distal end beyond the base point can be determined at all times.

The method of this embodiment enables three-dimensional device localization during an interventional procedure using only a single projection imaging, during at least the later part of the interventional procedure. In some cases, it may be difficult for a physician to become or remain oriented in a three dimensional (3D) setting using a display of a single-plane image projection. Further, the precise navigation of a medical instrument to target points within the patient, such as points on the cardiac wall, might be difficult in the absence of specific landmarks, or due to the viewing of such landmarks in projection view. Accordingly, enhancement or augmentation of the single-plane projection image may be required to aid the physician in visualizing the relative position and orientation of the medical device with respect to three-dimensional context such as tissue surfaces and organs in the body. The time-sequence of the control vector is in turn adjusted to navigate the medical device distal end to selected target points within the anatomy, and the device control can be effected either by the physician or through a close-loop algorithm by computer control of the device state variables.

In one embodiment of a method for localization utilizing a two-dimensional X-ray projection image, the method comprises the step of identifying the three-dimensional location of a base point from which a length of a medical device bends, together with the three dimensional base orientation of the device at the base point. Together with knowledge of the currently applied control vector, the three dimensional base orientation defines a bending plane in which the medical device is contained. The method further identifies the location of the distal end of the medical device as projected onto a X-ray projection image, and determines a point on a line between the X-ray source and device distal end projection on the X-ray imaging plane that is closest to the bending plane, for estimating the three-dimensional location of the end of the medical device. The method defines an expected two-dimensional location of the end of the medical device projected onto the X-ray projection image, as a function of the length of the medical device. From the expected two-dimensional location, the method determines a value of the length of the medical device that minimizes the distance between the identified two-dimensional location of the end of the medical device (as projected within the X-ray projection image) and the expected two-dimensional location calculated as a function of the length of the medical device. The method then determines a point on the line between the X-ray source and X-ray imaging plane that minimizes the distance between the estimated three-dimensional location of the end of the medical device and a three-dimensional location of the end of the medical device calculated as a function of the selected value of the length of the medical device, to obtain a refined estimated three-dimensional location of the end of the medical device.

BRIEF DESCRIPTION OF THE DRAWINGS

Corresponding reference numerals indicate corresponding points throughout the several views of the drawings.

DETAILED DESCRIPTION

In a catheterization laboratory ("cath lab") a remote navigation system can drive or control a medical device such as a sheath, a catheter, or a guide wire, either under direct physician control through a graphical user interface (GUI) in open-loop form or automatically to desired target locations in closed-loop form. Typically an X-ray fluoroscopic system is used in the cath lab to monitor device position relative to anatomy; thus, and for illustration, in cardiac applications such as electrophysiology the device position relative to the heart in a given x-ray image provides anatomical context. The physician can indicate desired target locations or targets to drive the device to by marking such targets on a pair of fluoroscopy images to define three dimensional points. To improve the work-flow, a method of estimating current device location and orientation in 3D space ("localization") is needed, preferably directly from a single X-ray projection to alleviate the need to rotate the imaging chain. With such information, an open-loop algorithm can be designed whereby the relative 3D information of the device and target point is displayed to the user, to more effectively steer the device to desired targets. Likewise closed-loop methods can also be designed, whereby the relative 3D information of the device and target point is input to a control algorithm that automatically navigates the device to the target. Localization enables shorter, more accurate and less invasive navigation to and within the organ of interest. The following descriptions of various embodiments are merely exemplary and are not intended to limit the invention, its application, or uses.

Figure 1:
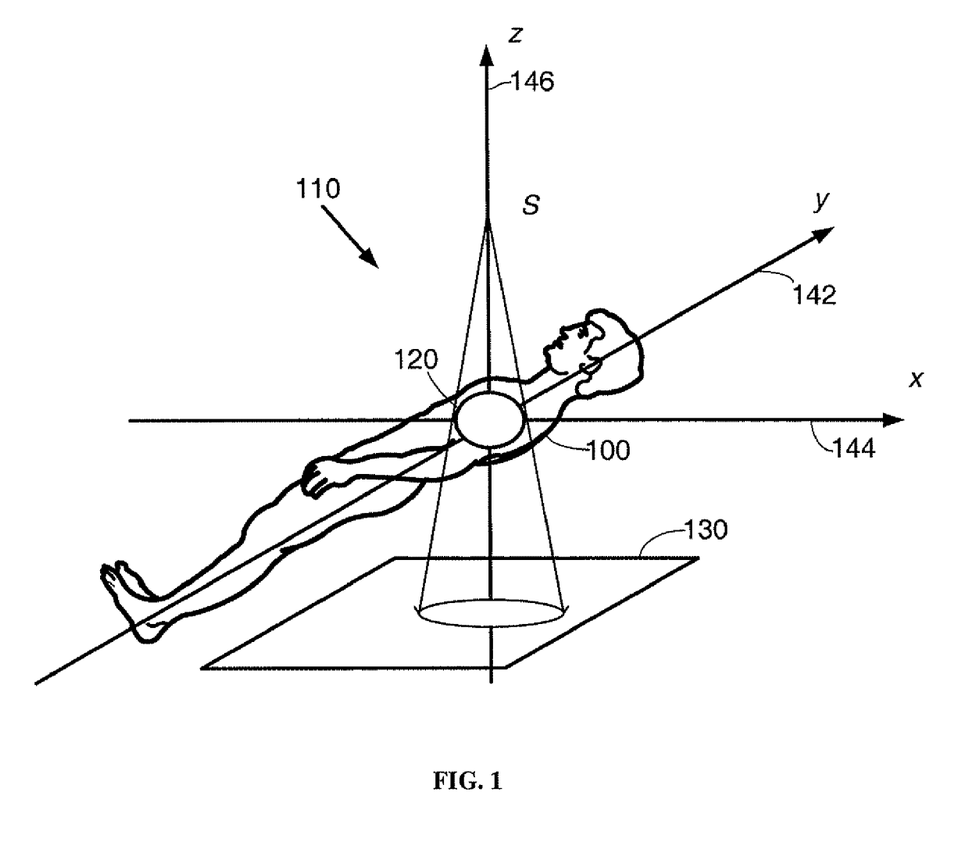
FIG. 1 shows a patient positioned in a projection imaging system for an interventional procedure using a controlled minimally invasive modality.

FIG. 1 shows a patient 100 positioned into a real-time projection imaging system 110 such as an X-ray fluoroscopy imaging chain. The patient positioning is such that an organ of interest 120 projects onto the detector 130. In a typical cardiac imaging system, the imaging chain can rotate with respect to the patient longitudinal axis y 142 to acquire projection data at a multiplicity of angles θ. The projection shown in FIG. 1 corresponds to the anterior-posterior projection, also retained to define the zero of the imaging chain projection angle (θ=0). In a typical cardiac examination, the patient lies supine on the examination table, and the axes x, 144, y, 142, and z, 146, respectively define the right-left lateral, inferior-superior, and posterior-anterior directions.

Figure 2:
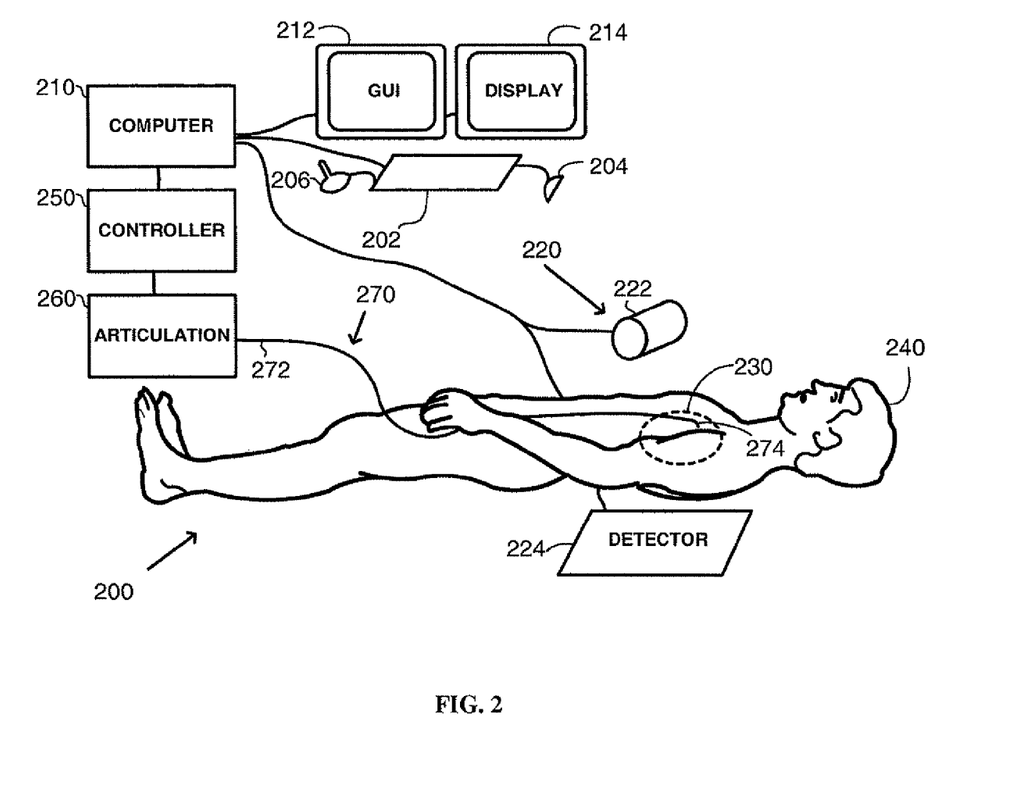
FIG. 2 is a system diagram for an interventional system designed according to the principles of the present invention and using a mechanically controlled modality.

FIG. 2 presents a system diagram for a preferred embodiment of an interventional system designed according to the principles of the present invention and using a mechanically controlled modality. One exemplary embodiment of such a system for navigating a medical device is indicated generally in FIG. 2 by reference number 200. A physician may use a keyboard 202, mouse 204, joystick 206, and/or other device to input instructions to a computer 210. The physician may also use a graphical user interface 212 and a display 214 connected with the computer 210 to monitor navigation and to operate the system 200. An imaging apparatus generally indicated in FIG. 2 by reference number 220 processes signals from the computer 210, acquires image data for an operating region 230 of a patient 240, and presents the corresponding images on the display 214. As an example, the imaging apparatus 220 may comprise an X-ray tube 222 and an X-ray detector 224 for the acquisition of radiographic or fluoroscopic images.

A controller 250 connected with the computer 210 controls an articulation mechanism 260 that translates and/or rotates a medical device 270 having a proximal end 272 and a distal end 274. The medical device 270 may be, for example, a catheter, guide wire, sheath, endoscope, or other device that the physician wishes to navigate in the patient's body. Additionally, the articulation mechanism 260 may operate a number of medical device internal pull-wires (not shown). These pull-wires extend through a tubular member of the medical device and terminate at various points along the device length. Articulation and control of the pull-wires enables local device bending and orientation, including at the device distal end, according to known device mechanical properties and device responses to known pull wires inputs ("transfer function").

Figure 3:
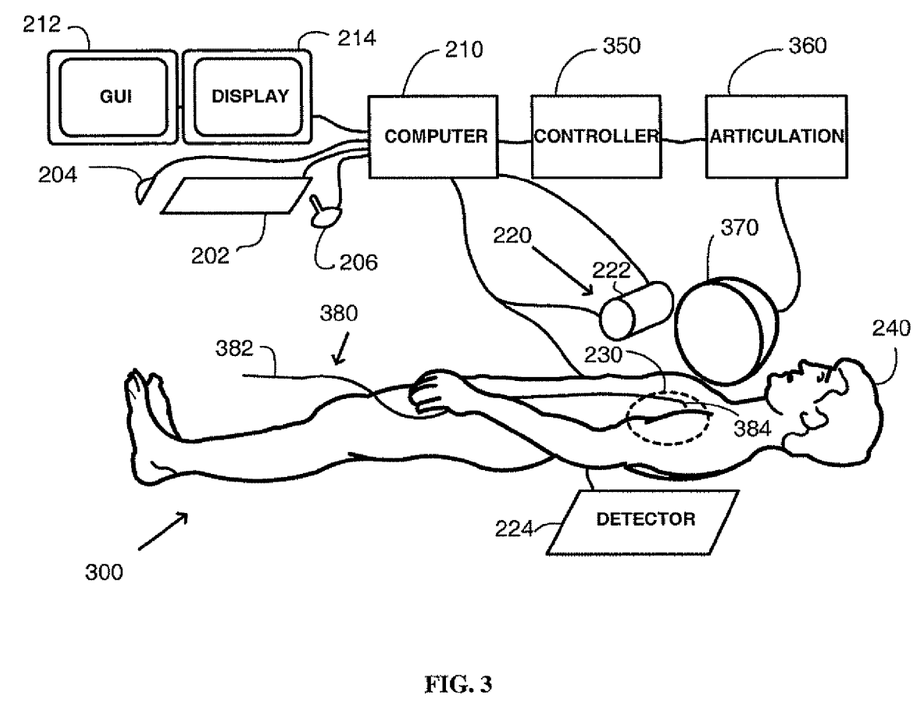
FIG. 3 is a system diagram for an interventional system designed according to the principles of the present invention and using a magnetically controlled modality.

FIG. 3 is a system diagram for an interventional system designed according to the principles of the present invention and using a magnetically controlled modality. One exemplary embodiment of a system for navigating a medical device is indicated generally in FIG. 3 by reference number 300. A physician may use a keyboard 202, mouse 204, joystick 206, and/or other device to input instructions to a computer 210. The physician may also use GUI 212 and display 214 connected with the computer 210 to monitor navigation and to operate the system 200. An imaging apparatus 220 processes signals from the computer 210, acquires image data for an operating region 230 of a patient 240, and displays the corresponding images on the display 214. As an example, the imaging apparatus 220 may comprise an x-ray tube 222 and an x-ray detector 224 for the acquisition of radiographic or fluoroscopic images.

A controller 350 connected with the computer 210 controls an articulation mechanism 360 that translates and/or rotates one or more source magnet(s) 370. The source magnet(s) 370 create a magnetic field of specific magnitude and orientation in the patient operating region 230 to control the orientation and translation of a medical device 380 having a proximal end 382 and a distal end 384. The distal end 384 comprises a magnetic tip 386 (not shown in FIG. 3). The source magnet(s) 370 may include permanent magnet(s) and/or electromagnet (s).

The medical device 380 may be, for example, a catheter, guide wire, sheath, endoscope, or other device that the physician wishes to navigate in the patient's body. The magnetic tip 386 may comprise one or more permanent or permeable magnets (not shown in FIG. 3) responsive to a magnetic field and/or gradient from the source magnet(s) 370. Articulation and control of the magnet(s) enables local device bending and orientation, including at the device distal end, according to known device mechanical and magnetic properties and device responses to known magnetic field inputs ("transfer function").

It will be clear to those skilled in the art that additional embodiments may be obtained by combining features of the systems presented in FIGS. 2 and 3. As an example, it might be desirable to automatically control the mechanical advance and rotation of the device proximal end, as well as automatically control the device pull-wires, in a magnetic navigation system. Such an embodiments, and other obtained by combinations of the invention features, are within the scope of the present invention.

Figure 4:
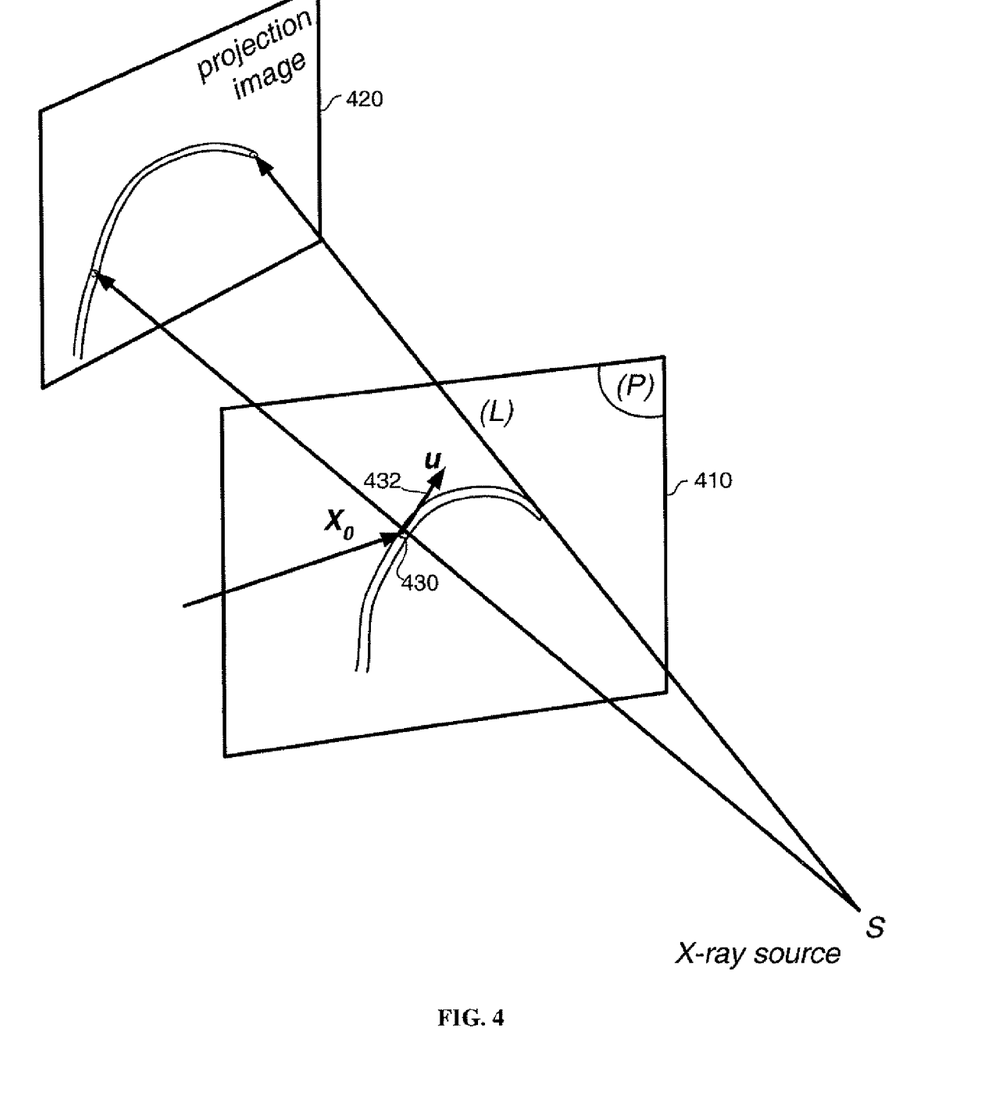
FIG. 4 is a diagram showing the projection of a catheter distal end where the controlled interventional modality is mechanical catheter navigation.

FIG. 4 presents a plane (P) 410 through a three-dimensional volume of an operating region of a patient placed within a mechanical navigation system, and an associated x-ray projection 420. The remote navigation system is a mechanical navigation system controlled by externally applied forces and torques. Additionally, such a device may also be controlled by a number of wires internal to the device and terminating at various locations along the device. The present invention can also be applied to navigation of devices using electrostriction, hydraulic actuation, or other device control modalities. It is assumed that the base of the device, i.e., the position $X_0$ 430 of the point of support and its orientation u 432 (unit vector), are known. The base, or point of support, defines a location within the patient from which the device progress will be monitored and controlled by use of a single x-ray projection. Typically, the base information is derived from an acquisition of two or more projections. Subsequent to base data acquisition, the imaging chain remains at a fixed angle with respect to the patient. Knowledge of the device mechanical properties allows defining a transfer function that uniquely describes the response of the device to changes in the control variables ("control state"). Accordingly, from a knowledge of the base point three-dimensional location 430, observation of the device position with respect to the anatomy (in the single two-dimensional X-ray projection), and knowledge of the control state of the device over time, the position and orientation of the device distal end can be known at all times.

Figure 5:
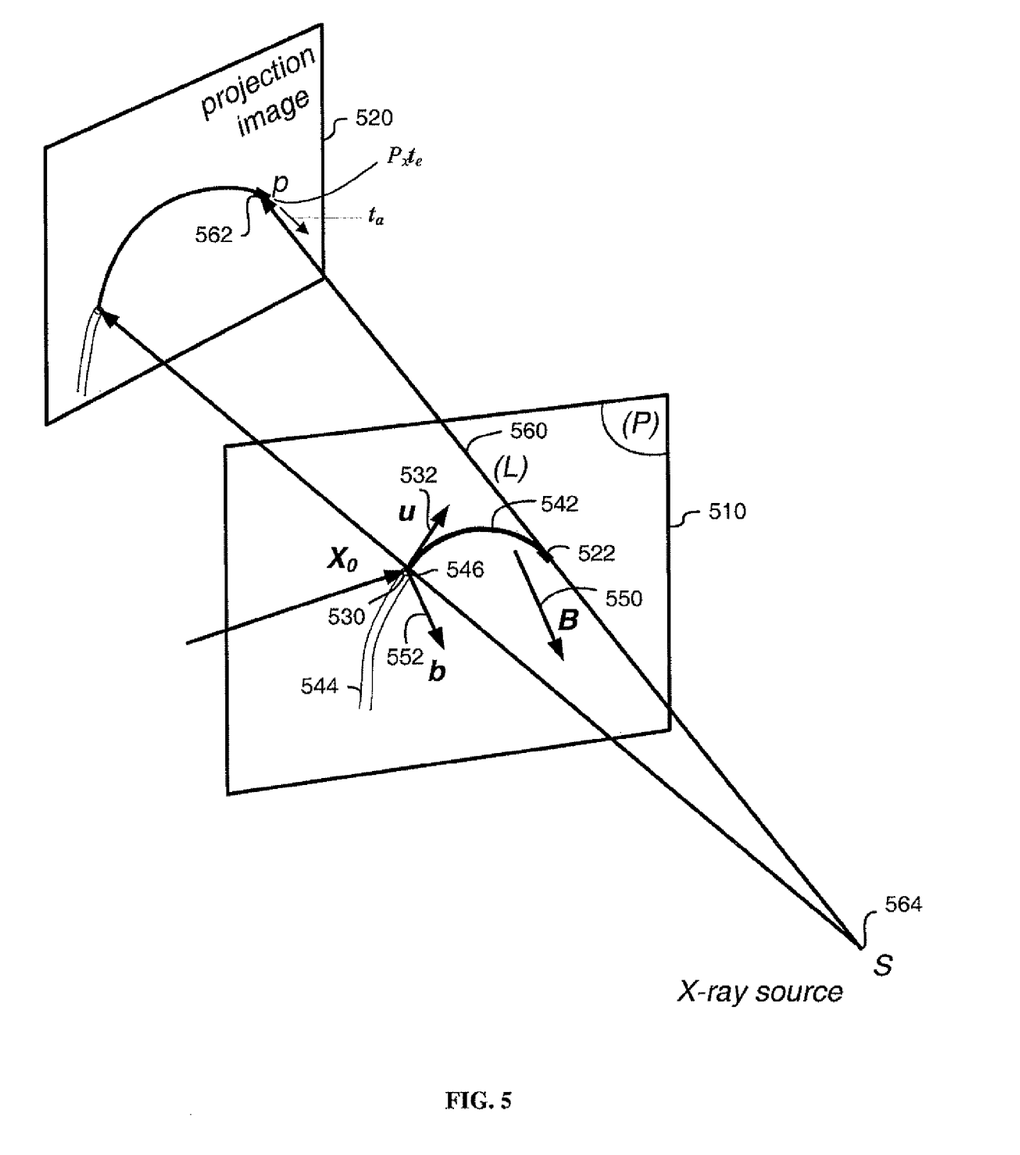
FIG. 5 is a diagram showing the projection of a guide wire distal end and guide wire magnetic tip where the controlled interventional modality is magnetic navigation.

Further illustration of this concept is presented in FIG. 5. FIG. 5 shows a plane (P) 510 through a 3D volume of an operating region of a patient placed within a magnetic navigation system, and an associated x-ray projection 520. The magnetic navigation system illustrated in FIG. 5 controls externally applied magnetic fields that orient a device tip magnet m 522. Again it is assumed that the base information for the device distal end (including point of support position and orientation) is known. Let the base point of support in 3D space be denoted by $X_0$ 530, and u 532 (3D unit vector) represent the orientation of the device or of a device support sheath at $X_0$ (FIG. 5 shows a guide wire 542 being advanced through a sheath 544, the sheath distal end 546 being coincident with the device base 530). Let B 550 be the applied magnetic field (with magnitude B and direction b 552 (unit vector). As the torque γ applied by B to the device tip magnet m 522 is given by $\vec{\gamma} = \vec{m} \times \vec{B}$, the normal n to the device bending plane (P) 510 is:

$$\vec{n} = \frac{\vec{u} \times \vec{b}}{\|\vec{u} \times \vec{b}\|}, \tag{1.1}$$

where the normalized cross-product defines the unit vector n. In FIG. 5 the device bending plane (P) including the base $X_0$ is shown. It is noted that the three-dimensional location of the magnetic catheter distal end 522 can lie anywhere along line (L) 560 between location p 562 on the projection image and the X-ray source S 564. The localization method proceeds through the following steps.

First a point $X_m$ is found that defines the center of a 3D neighborhood volume over which subsequent optimization occurs. Then, a point $X_m$ on line (L) is found that minimizes the cost function q:

$$q(\vec{X}) = \|(\vec{X} - \vec{X}_0) \cdot \vec{n}\|. \tag{1.2}$$

Accordingly, a point $X_m$ on (t) that is closest to the natural bending plane (P) of the device can be found.

Figure 6:
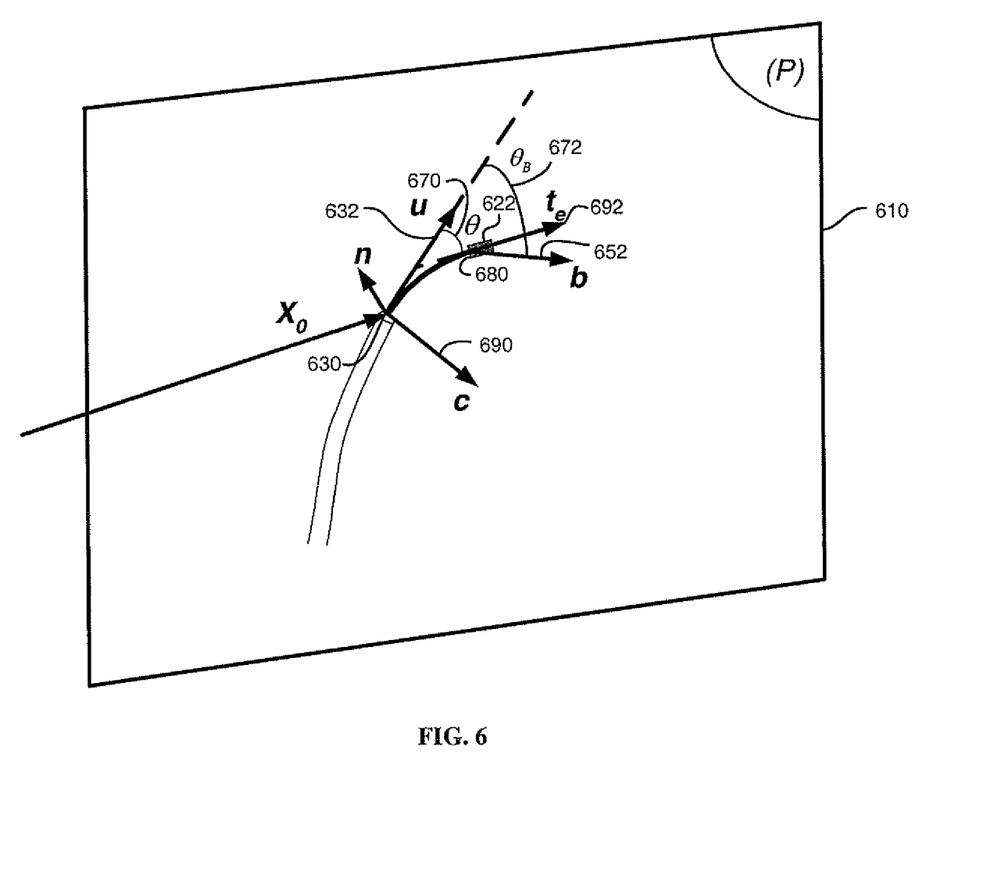
FIG. 6 is a diagram showing the coordinates for the device bending plane (P) and angles of applied magnetic torque and mechanical torque within the bending plane.

In the second step the length l of the device out from the base point 630 is determined. Referring now to FIG. 6 showing the bending plane (P) 610 and the base point $X_0$ 630, let θ 670 be the tip deflection of the device (angle made by device tip 622 with base vector u 632), and $θ_B$ 672 be the angle between u 632 and b 652. If E is the Young's modulus of the device shaft and I its bending moment of inertia, m the magnetic moment at the catheter tip (of modulus m), then the torque τ exerted on the catheter by the magnetic moment is given by the equation:

$$\tau = m \times B \times \sin(\theta_B - \theta) = \frac{E \times I}{l} \times \theta, \tag{1.3}$$

where l is the length of the flexible shaft from the base point $X_0$ 630 to the proximal tip magnet end 680. Defining vector c 690:

$$\vec{c} = \vec{n} \times \vec{u}, \tag{1.4}$$

which is the unit vector perpendicular to u in the bending plane (P), the expected (estimated) three-dimensional distal end orientation t, 692 is given by:

$$\vec{t}_e = \cos(\theta)\vec{u} + \sin(\theta)\vec{c}. \tag{1.5}$$

The expected two-dimensional catheter distal end projected onto the X-ray plane (not shown in FIG. 6, see FIG. 5) is then given by ($P_X \vec{t}_e$), where $P_x$ is the projection operator associated with the projection geometry. Let $t_a$ be the unit vector corresponding to the catheter end in the X-ray image. This can be either identified or marked by the user on a navigation user interface, or it can be identified from the two-dimensional X-ray image automatically using an image processing algorithm. Once $t_a$ is identified, a measure of distance (cost or error) between $t_a$ and $P_x t_e$ can be defined. It is noted that E, I, m, B, and $θ_B$ being known, a given value of the length l determines a value of θ in equation (1.3), and thence determines $t_e$ from equation (1.5). Thus the expected 2D catheter distal end orientation, $P_x t_e$, can be calculated for a given l value. By searching within a range associated with the neighborhood of $X_m$ (the previously defined center of a 3D neighborhood volume), a value l* of l is found that minimizes the cost function:

$$\|P_x \vec{t}_e - \vec{t}_a\|. \tag{1.6}$$

According to the device mechanical model, the length l* is that of an arc of circle; therefore the location y of the catheter distal end in 3D space is given by:

$$\vec{y} = \vec{X}_0 + \frac{l^*}{\theta}[\sin(\theta)\vec{u} + (1 - \cos\theta)\vec{c}] + l_m \vec{t}_e, \tag{1.7}$$

where $l_m$ is the length to the tip magnet. In a third step, a cost function C(X) is defined by:

$$C(\vec{X}) = \|\vec{y}_t - \vec{X}\|, \tag{1.8}$$

where X is a point in a pre-determined neighborhood of $X_m$, the point X=X* is selected such that C is minimized; X* is the estimated 3D-localized catheter tip location. To refine the catheter tip location estimate, the two steps above of finding l* and then finding X* are repeated until such a C-minimizing X* is found.

In an alternate optimization algorithm, the cost function:

$$D[\vec{X}(l)] = \alpha \left\| P_x \vec{t}_e - \vec{t}_a \right\|^\gamma + \beta \left\| \frac{\vec{y}_t - X}{l} \right\|^\delta \qquad (1.9)$$

is defined and the estimate X* is found that minimizes D. Such an approach blends minimization of the 3D distance between the estimate X* and the device tip yt and the minimization between these two points as projected onto the X-ray detector. The parameters $\alpha$, $\beta$, $\gamma$, and $\delta$ allow fine-tuning of the optimization algorithm by weighting and tailoring these two cost function components.

As described above, a computational model of the flexible medical device can be used to estimate 3D device distal end position starting from a single X-ray projection. Once the 3D location X* is determined, this information can be used to automate navigation to any desired target location T by successively driving the catheter closer to T with a feedback-control algorithm. Thus, fluoroscopy-based closed-loop catheter control becomes possible. It is clear that the method above can be extended to devices with variable properties along the length, such as variable stiffness and/or variable thickness. Further, the method generally applies whenever a transfer function can be derived that describes the device shape as a function of control variables (or state vector).

Figure 7:
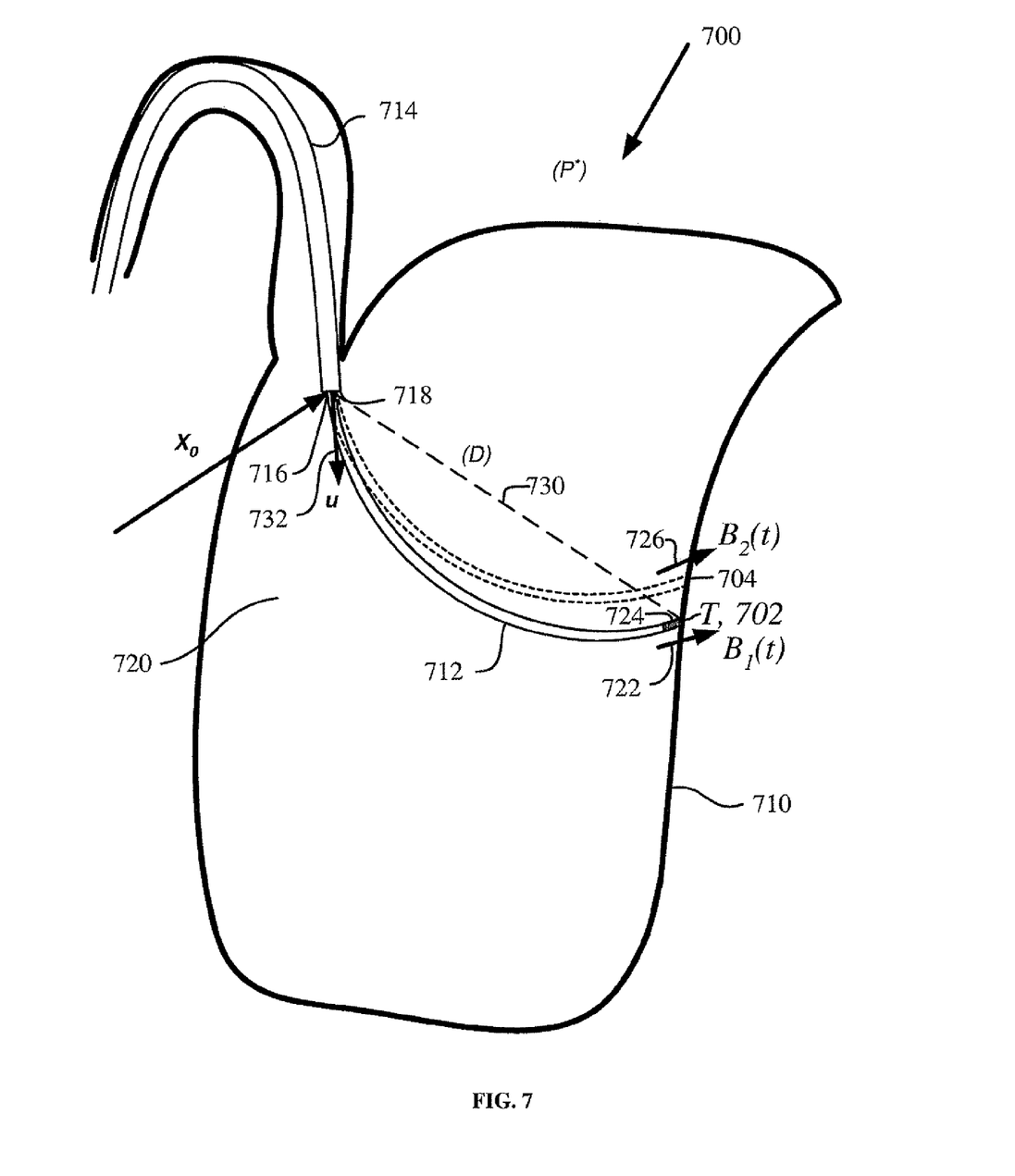
FIG. 7 is a diagram showing navigation of a medical device to multiple anatomy target points according to the principles of the present invention.

Target locations can also be selected on a 3D pre-operative image, and after the 3D image is registered to fluoroscopy projections, closed-loop navigation to targets chosen on the 3D image becomes possible using the techniques described in the embodiments of the present invention. FIG. 7 illustrates navigation of a medical device distal end to a series of target locations. In FIG. 7, a sequence of user or computer-identified target points 702, 704 . . . , on the cardiac wall 710 is input to the navigation algorithm. A medical device 712 is advanced through a sheath or catheter 714 previously navigated to a base point $X_0$ 716. The device tip progresses past the sheath distal end 718 and through the cardiac chamber 720. A first sequence of magnetic fields $B_1(t)$ 722 is applied at the magnetic tip 724 to steer the device to the first target point T 702. The device is then retracted in part or all the way to base point 716, and a second sequence of magnetic fields $B_2(t)$ 726 is applied to guide the device to the second target point 704, and so on for the entire set of identified target points. FIG. 7 also shows line (D) 730 joining $X_0$ and T; the plane (P*) containing (D) and u 732 is a likely choice for device navigation to target point T. FIG. 7 presents a cross-section along plane (P*), and (P*) is shown for illustration to also contain target point 704 and the device sheath 714; in general that will not be the case.

Figure 8:
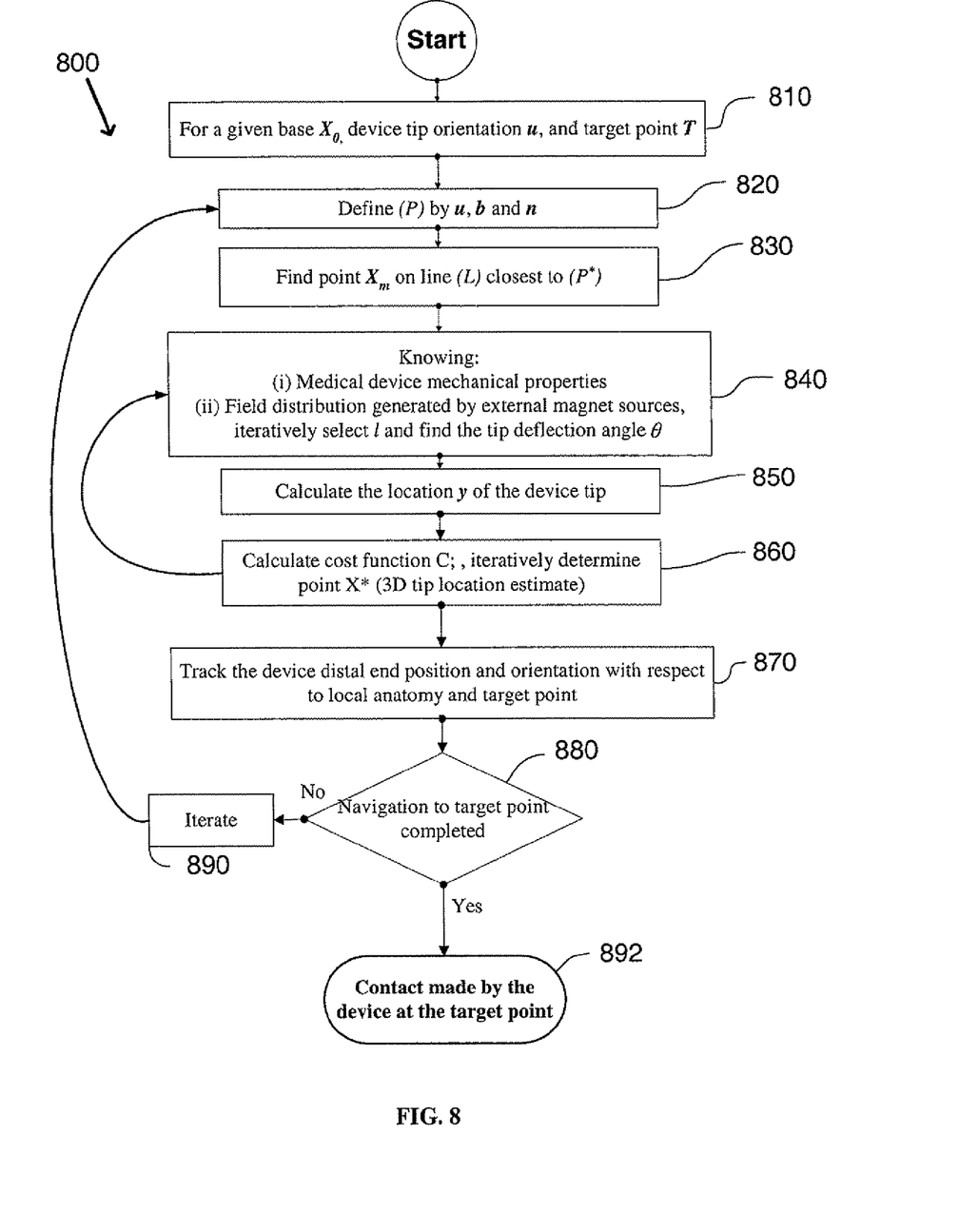
FIG. 8 is a flow-chart diagram for one embodiment of the present invention.

FIG. 8 is a method flow-chart for one embodiment of the present invention. The method proceeds in steps, generally indicated by numeral 800, described below. In the first step 810, the method proceeds for a given, known, base point position $X_0$ and orientation u and considers one point T of a set of identified target points. Through the line connecting $X_0$ and T pass an infinite number of planes; one of these, plane (P*), contains vector a representing the device distal end orientation at $X_0$, and defines a likely choice for navigation of the device from $X_0$ to T. With such a choice, the applied navigation field B(t) always lie within plane (P*). In step 830, the point $X_m$ on line (L) joining the source to the device tip X-ray projection is found that is closest to (P*); in the majority of the cases, $X_m$ will lie on or near (P*) within the computer precision. In steps 840, 850, and 860, the method iteratively determines optimum point X* that minimizes the cost function C. Knowing (i) the medical device mechanical properties and (ii) the local magnetic field distribution generated by external sources, we can iteratively refine the value of l to find tip deflection angle θ. This is done by choosing a values for l in a given range, calculating the associated device bending angle θ and device distal end 3D position, and calculating the associated cost function C in the projection plane, and iterating over l in a range of values to refine the X* estimate. The knowledge of estimate X* allows tracking of the device distal end position and orientation with respect to anatomy and target point T, step 870. Tracking and navigation can be done either under physician control or automatically under computer closed-loop control. The physician or computer select the magnetic field magnitude and orientation, proximally advance the device, and iteratively track progress to the target point, steps 880 and 890. Navigation to the target point is complete upon device contact, step 892. The steps described above are repeated for each point within a set of target points. This set can be preidentified, or identified or modified during the intervention.

Examples of models for predicting the three dimensional configuration of the distal end portion of a medical device are disclosed in U.S. patent application Ser. No. 10/448,273, filed May 29, 2003, entitled Remote Control of Medical Devices Using a Virtual Device Interface, and U.S. Provisional Patent Application No. 60/401,670, filed Aug. 6, 2002, and U.S. Provisional Patent Application Ser. No. 60/417,386, filed Oct. 9, 2002, entitled Method and Apparatus for Improved Magnetic Surgery Employing Virtual Device Interface, the disclosures of all of which are incorporated herein by reference.

The advantages of the above described embodiment and improvements should be readily apparent to one skilled in the art, as to enabling the determination of a medical device distal end location and orientation from a single image projection. Additional design considerations may be incorporated without departing from the spirit and scope of the invention. Accordingly, it is not intended that the invention be limited by the particular embodiment or form described above, but by the appended claims.

What is claimed is:

1. A method of estimation of three-dimensional localization information for a medical device distal end utilizing a two-dimensional X-ray projection image, the method comprising:
   identifying the three-dimensional location of a base point from which a length of medical device bends, and a three dimensional orientation vector for the device at the base point;
   defining a bending plane in which the medical device is contained;
   identifying the location and orientation of the end of the medical device as projected onto a X-ray projection image;
   determining a line between the X-ray source and X-ray imaging plane for use in estimating the three-dimensional location of the end of the medical device;
   defining an expected two-dimensional orientation of the end of the medical device projected onto the X-ray projection image, as a function of the length of the medical device;

determining a value of the length of the medical device that minimizes the deviation between the identified two-dimensional orientation of the end of the medical device as projected onto the X-ray projection image and the expected two-dimensional orientation calculated as a function of the length of the medical device; and determining a point on the line between the X-ray source and X-ray imaging plane that minimizes the distance between the line and a three-dimensional location of the end of the medical device calculated as a function of the selected value of the length of the medical device, to obtain a refined estimated three-dimensional location of the end of the medical device.

2. The method of claim 1, wherein the method for estimation of the three-dimensional location of a medical device is utilized in a feedback control algorithm for improving accuracy in navigating the end of a medical device to a target area within a subject body.

3. The method of claim 1 wherein the expected two-dimensional orientation of the end of the medical device is further calculated as a function of the device's mechanical properties.

4. The method of claim 3 wherein the mechanical properties include the modulus of elasticity, the bending moment of inertia, and the length of the bend in the medical device.

5. The method of claim 1 wherein the two-dimensional x-ray image is a projection image in an x-ray imaging system.

6. The method of claim 1 wherein the method of estimation comprises using a transfer function for the medical device.

7. The method of claim 6 wherein the transfer function relates output parameters comprising local shape and local orientation at a number of points along the device to input parameters comprising pull wire tensions.

8. The method of claim 6 wherein the transfer function relates output parameters comprising local shape and local orientation at a number of points along the device to input parameters comprising magnetic field distributions.

9. The method of claim 6 wherein the transfer function relates output parameters comprising local shape and local orientation at a number of points along the device to input parameters comprising applied voltages.

* * * * *